US007226423B2

(12) United States Patent
Goldenberg

(10) Patent No.: US 7,226,423 B2
(45) Date of Patent: Jun. 5, 2007

(54) ASPIRATION NEEDLE WITH VENTING FEATURE

(76) Inventor: Alec S. Goldenberg, 157 E. 32nd St., New York, NY (US) 10016

( * ) Notice: Subject to any disclaimer, the term of this patent is extended or adjusted under 35 U.S.C. 154(b) by 180 days.

(21) Appl. No.: 10/971,302

(22) Filed: Oct. 22, 2004

(65) Prior Publication Data

US 2006/0089567 A1  Apr. 27, 2006

(51) Int. Cl.
 A61B 10/00 (2006.01)
 A61B 5/00 (2006.01)
 A61M 3/00 (2006.01)
(52) U.S. Cl. .................. 600/562; 600/564; 600/573; 604/45
(58) Field of Classification Search ........ 600/562–567; 604/43–45
See application file for complete search history.

(56) References Cited

U.S. PATENT DOCUMENTS

| | | | |
|---|---|---|---|
| 2,409,343 A | 10/1946 | Curtis | |
| 2,541,272 A * | 2/1951 | Murphy | ..................... 141/285 |
| 2,989,053 A | 6/1961 | Hamilton | |
| 3,063,451 A | 11/1962 | Kowalk | |
| 3,484,849 A | 12/1969 | Huebner et al. | |
| 3,662,752 A | 5/1972 | Yokoyama | |
| 3,797,521 A | 3/1974 | King | |
| 3,872,730 A | 3/1975 | Ringrose et al. | |
| 3,938,520 A | 2/1976 | Scislowicz et al. | |
| 4,058,121 A | 11/1977 | Choksi et al. | |
| 4,118,987 A | 10/1978 | Zeh | |
| 4,211,588 A | 7/1980 | Raines | |
| 4,296,786 A | 10/1981 | Brignola | |
| 4,461,185 A | 7/1984 | Schoffel | |
| 4,505,709 A | 3/1985 | Froning | |
| 4,507,113 A | 3/1985 | Dunlap | |
| 4,532,969 A | 8/1985 | Kwaan | |
| 4,534,758 A | 8/1985 | Akers et al. | |
| 4,588,403 A * | 5/1986 | Weiss et al. | ................. 604/411 |
| 4,610,683 A | 9/1986 | Vaillancourt | |
| 4,651,574 A | 3/1987 | Spencer | |
| 4,787,898 A | 11/1988 | Raines | |
| 4,791,821 A | 12/1988 | Spencer | |
| 4,808,157 A * | 2/1989 | Coombs | ....................... 604/44 |
| 5,012,818 A * | 5/1991 | Joishy | ........................ 600/567 |
| 6,221,622 B1 | 4/2001 | Love | |
| 6,494,859 B2 | 12/2002 | Love | |
| 6,730,045 B2 | 5/2004 | Finer | |
| 7,014,622 B1 * | 3/2006 | Pressly et al. | .............. 604/110 |

* cited by examiner

Primary Examiner—Max Hindenburg
Assistant Examiner—Jonathan Foreman
(74) Attorney, Agent, or Firm—Darby & Darby

(57) ABSTRACT

An aspirating needle for collecting a specimen including an elongated hollow body that includes a first lumen portion and a second lumen portion. The first lumen portion is open at both ends for placement at a specimen site to collect and permit aspiration of the specimen from the specimen site. The second lumen has first and second vent ports, with the second vent port being formed along the elongated body such that that when the needle is placed at the specimen site, the second vent port is positioned at the specimen site. The first vent port is in fluid communication with atmospheric air when the needle is positioned at the specimen site so as to permit pressure within the specimen site to equilibrate with atmospheric pressure by means of the venting action of the second lumen.

8 Claims, 3 Drawing Sheets

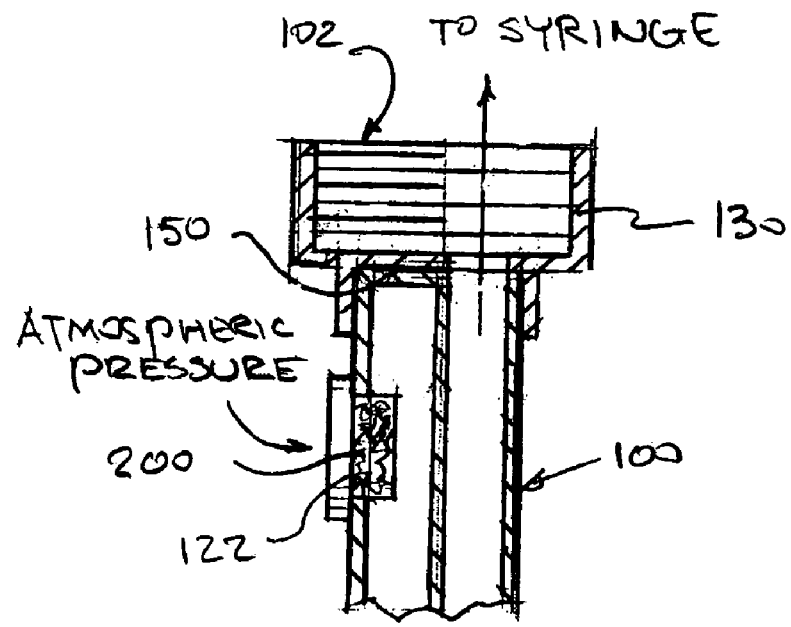
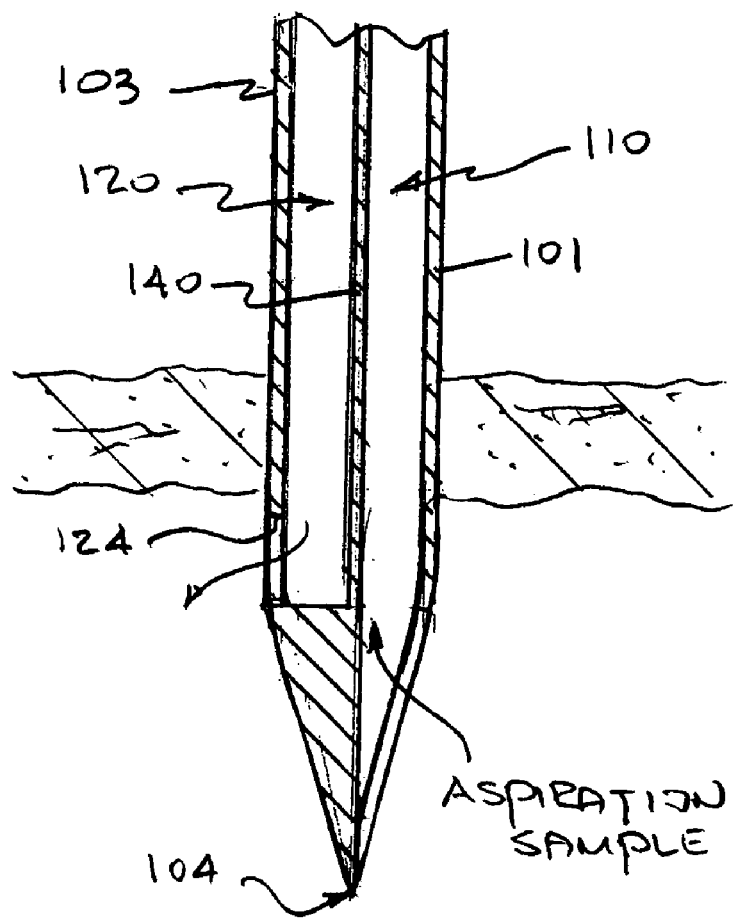
FIG 2

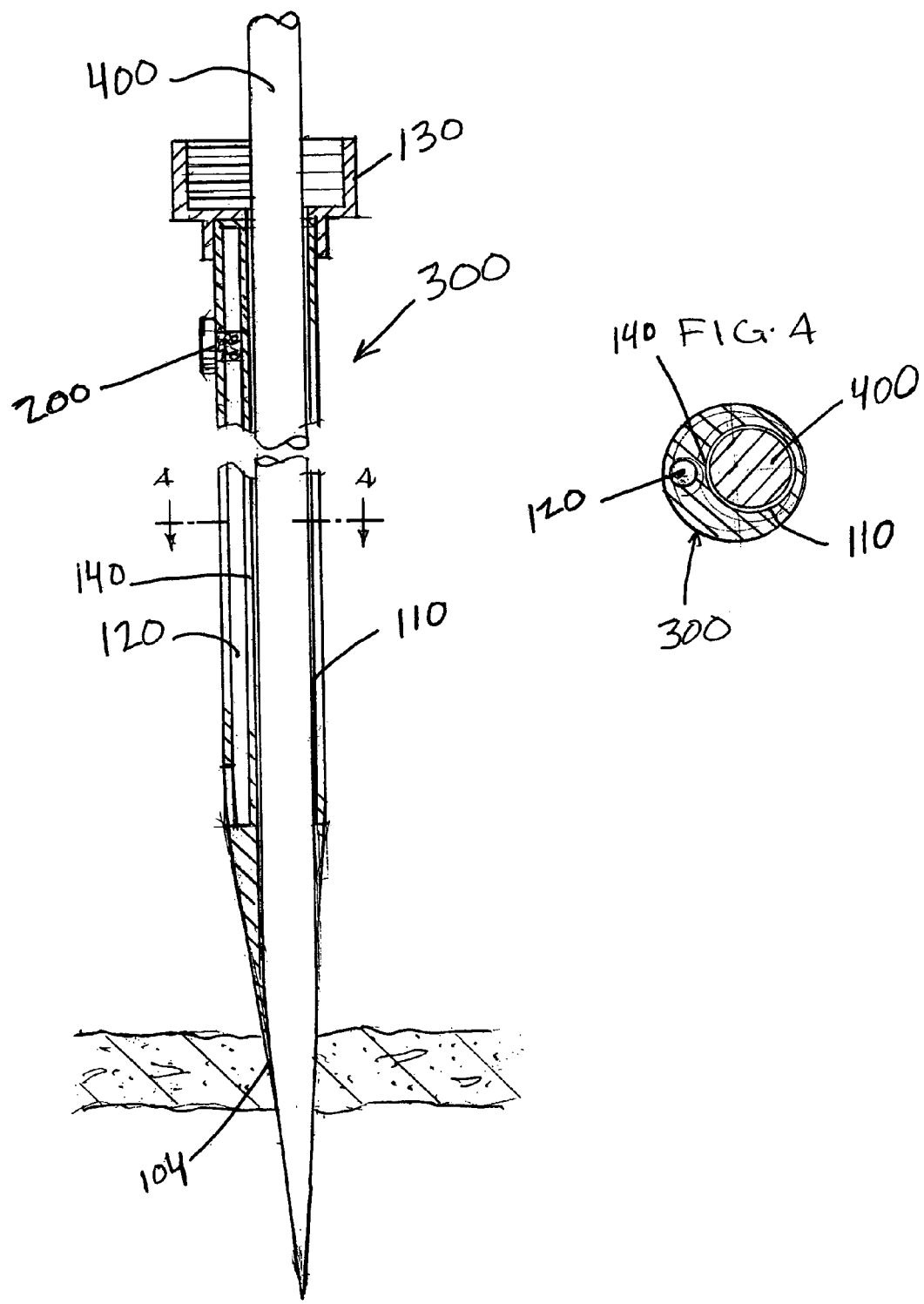

ASPIRATION NEEDLE WITH VENTING FEATURE

TECHNICAL FIELD

The present invention relates to an instrument, typically known as a needle or cannula that is used to gather a sample from a site using aspiration and more particularly, relates to an aspiration needle for gathering tissue from living persons or animals for pathological study and includes an improved structure for collecting a fluid sample of bone marrow.

BACKGROUND

For various medical reasons, such as diagnostic tests or the like, it is often necessary for a physician to obtain a sample of a specific tissue from a patient Often, it is required to take a biopsy (sample) from a rigid structure, such as a bone or bone marrow. Bone marrow biopsies are typically recovered with significant portions of their internal bony structure intact which allows the pathologist to provide interpretations regarding bone marrow cellularity or possible infiltration with abnormal cells.

A bone marrow sampling procedure usually includes both the collection of a core biopsy using a bone marrow biopsy needle and a fluid sample of bone marrow using an aspiration needle. The two specimens provide complementary information that is relevant for the evaluation of a variety of malignant and nonmalignant hematologic processes. The bone marrow aspiration provides a liquid sample of suspended hematopoietic progenitor cells, stromal cells, and trabecular bone fragments that can be processed for flow cytometric analysis of the bone marrow content, for cytogenetic studies, as well as for the preparation of smears for detailed morphologic evaluation of the progenitor cell morphology. The core biopsy provides accurate information regarding the status of the supporting bone, the cellularity of the bone marrow sample, and the identification of extrinsic cells as seen when the bone marrow is infiltrated with lymphoma or carcinoma.

The process of obtaining both the core biopsy and aspiration sample can produce significant pain for the patient. Specimen capturing needles, including those of the present applicant that are set forth in issued and pending applications, have been designed in an attempt to limit the manipulation of the bone marrow biopsy needle, to increase the recovery of more substantial specimens and to decrease patient pain. However, conventional needles have not been specifically designed to minimize the pain associated with the aspiration process.

Aspiration type needles have a relatively simple design. The needle typically has a sharp tip for puncturing the cortical bone and usually a hub and handle to facilitate the operators guiding the tip safely into the appropriate position. A stylet is left in place until the needle has penetrated the cortex, after which it is removed and an aspirating syringe is placed at the hub. The syringe plunger is rapidly withdrawn to quickly produce a negative pressure which is transmitted through the needle into the bone marrow space to dislodge the material and facilitate its collection into the syringe through the needle. The procedure of quickly pulling back on the plunger and producing a negative pressure usually produces significant pain often described as radiating down the leg. Since the advent of specimen capturing needles, the pain has been described by some patients as being worse than the pain associated with the bone marrow biopsy procedure. An aspirate needle that minimizes patient pain would make the bone marrow procedure more tolerable and acceptable. Moreover, an aspirate needle that minimizes pain would be especially advantageous when multiple aspirates are required to recover a sufficient quantity of bone marrow material for processing.

The exact mechanism that results in the pain and its radiation down into the lower extremity is unknown. It is hypothesized that the introduction of a negative pressure into the bone marrow space stimulates a variety of nerve fibers that results in the pain Alternatively, simple disruption of the trabecular structure may be the source of the pain.

SUMMARY

An aspirating needle for collecting a specimen is provided and includes an elongated hollow body that includes a first lumen portion and a second lumen portion. The first lumen portion is open at both ends for placement at a specimen site to collect and permit aspiration of the specimen from the specimen site. The second lumen has first and second vent ports, with the second vent port being formed along the elongated body such that that when the needle is placed at the specimen site, the second vent port is positioned at the specimen site. The first vent port is in fluid communication with atmospheric air when the needle is positioned at the specimen site so as to permit pressure within the specimen site to equilibrate with atmospheric pressure by means of the venting action of the second lumen.

The aspiration needle of the present invention finds particular utility in an application where tissue is gathered from living persons or animals for pathological study and more specifically, the venting feature of the needle provides an improved structure for collecting a fluid sample of bone marrow.

Other features and advantages of the present invention will be apparent from the following detailed description when read in conjunction with the accompanying drawings.

BRIEF DESCRIPTION OF THE DRAWING FIGURES

The foregoing and other features of the present invention will be more readily apparent from the following detailed description and drawings figures of illustrative embodiments of the invention in which:

FIG. 2 is a cross-sectional view of the aspiration needle of FIG. 1;

FIG. 3 is a cross-sectional view of an aspiration needle according to a second embodiment; and FIG. 4 is a cross-sectional view taken along the line 4—4 of FIG. 3.

DETAILED DESCRIPTION OF PREFERRED EMBODIMENTS

Figure 1:
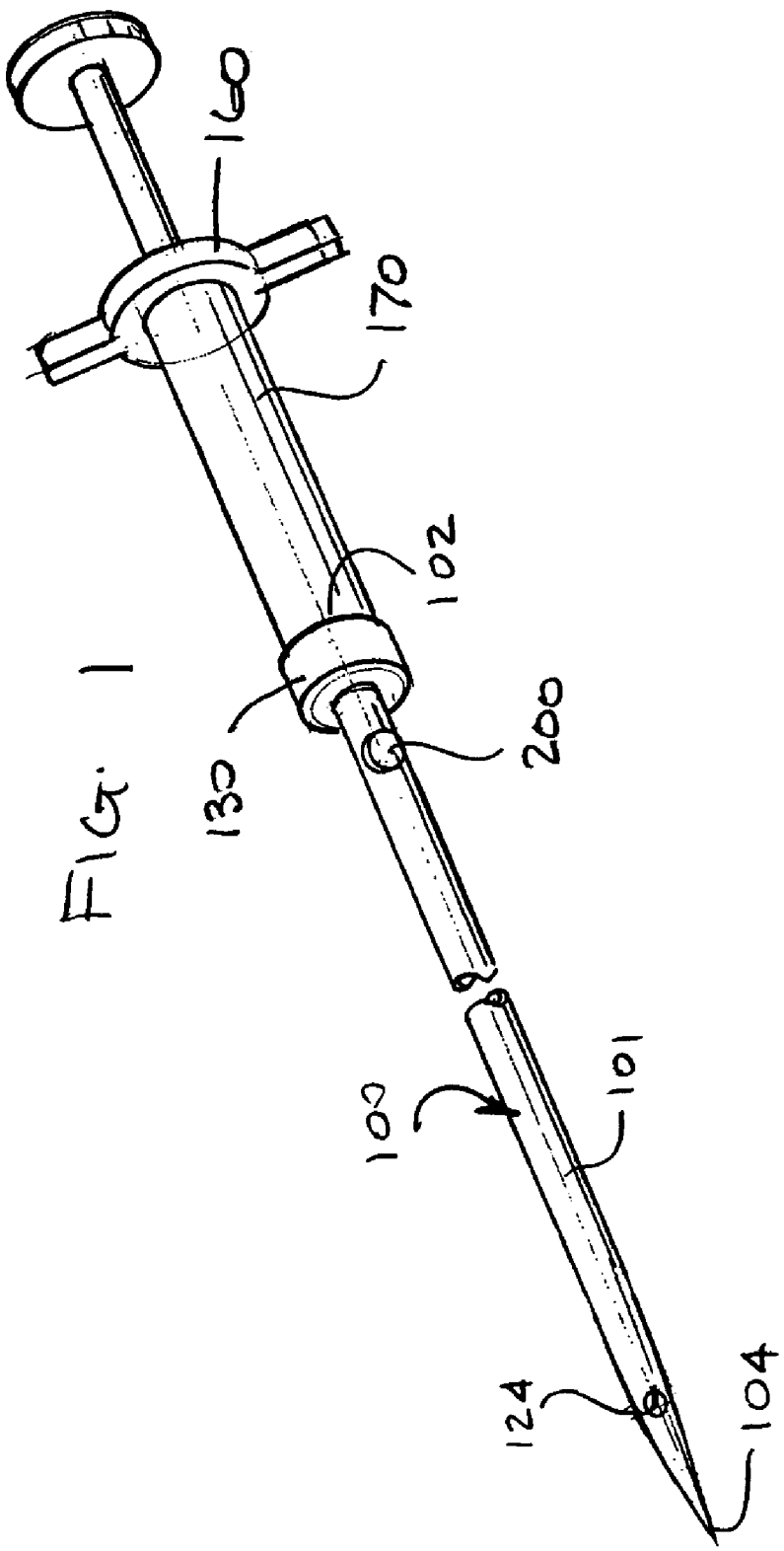
FIG. 1 is a perspective view of an aspiration needle according to a first embodiment for use at a site that is aspirated to collect a sample, such as a fluid sample of bone marrow.

Referring now to FIGS. 1 and 2, an aspiration needle 100 according to one exemplary embodiment is illustrated and is particularly suited for use at a target site, such as one associated with a bone marrow aspiration application. In other words, while the aspiration needle 100 is particularly suited for use in medical applications where aspiration of a local site takes place, it will be understood that the needle 100 is suited for other applications in which equilibration of the aspirated space is desirable. It is contemplated that there are additional non-medical applications for the aspiration needle 100 with one potential application being a manufacturing type application or a laboratory application where equilibration is needed.

The aspiration needle 100 is constructed to overcome the deficiencies associated with conventional bone marrow aspiration needles and more specifically, is constructed to minimize the potential negative pressure that develops during the bone marrow collection and aspiration process. In order to achieve this goal, the needle 100 includes a type of "vent" that modulates the pressure in the bone marrow space as the material is withdrawn.

The needle 100 has a first end 102 that is a proximal end and an opposing second end 104 that is a distal end. The second end 104 (distal end) is the sharp tip end for puncturing the cortical bone during the bone marrow collection procedure. The needle 100 is based on a double lumen design in that the needle 100 includes a first lumen 110 and a second lumen 120 that is proximate the first lumen 110. The first lumen 110 acts as a conduit for material to be withdrawn out of a bone marrow space into a syringe 160, while the second lumen 120 allows the pressures within the bone marrow space to equilibrate with outside pressures. The needle 100 is securely coupled to the syringe 160 using conventional techniques, such as threaded fastening means. The syringe 160 include a collection chamber 170 (barrel chamber) for collecting the sample that is aspirated through the needle 100.

The first end 102 has a feature 130 that permits the needle 100 to be coupled to another component and therefore, can include a flange, cap, coupling member or the like. The first end 102 can serve as or be coupled to a hub and handle to facilitate the operators guiding the second end 104 safely into the appropriate position. The needle 100 shares a number of characteristics that are basic to most needles in that that the needle 100 is defined by an elongated structure (body 101) that is hollow in nature from one end 102 to the other end 104. The needle 100 can have any number of different shapes and for purpose of illustration only, the illustrated needle 100 has a circular cross-section; however, it will be appreciated that the cross-section of the needle 100 can be other shapes, including but not limited to square shaped, rectangular shaped, triangular shaped, etc.

The division of the body 101 of the needle 100 can be accomplished in any number of different ways so long as the body 101 is divided into the first lumen 110 and the second lumen 120. For example, the needle 100 can include a dividing or partitioning wall 140 that is formed within the body 101 and serves to partition at least a length of the interior of the body 101 into the first and second lumens 110, 120. It will be appreciated that the wall 140 does not have to evenly divide the interior of the body 101 such that the first and second lumens 110, 120 occupy the same area but rather the first and second lumens 110, 120 can occupy different amounts of areas. Thus, while FIG. 1 shows the wall 140 generally evenly dividing the interior of the body 101 into the first and second lumens 110, 120, this is merely exemplary and illustrative in nature as opposed to being limiting. For example, the second lumen 120 that is associated with performing a venting operation can occupy less area than the first lumen 110 which serves as the conduit for withdrawing the bone marrow or sample material. Another embodiment is one where the divider 140 is eliminated and a tube, possibly flexible, is provided within the body of the needle 101 with one end of the tube exiting at the lumen 122 and the other exiting or connected to the lumen or vent 124.

The first lumen 110 is thus a generally unobstructed channel that extends from the first end 102 to the second end 104 and therefore, it permits material to be aspirated into the distal second end 104 and withdrawn to the first end 102 in a generally linear manner. Conversely, the second lumen 120 is not constructed to receive material at the bone marrow site (space) but rather, the second lumen 120 is constructed to permit atmospheric air to be delivered to the bone marrow site so as to serve as a vent and allow the pressure within the bone marrow space to equilibrate with outside pressures, e.g., atmospheric pressure.

In the illustrated embodiment, the second lumen 120 has a first open end 122 and an opposing open second end 124, with the first end 122 being proximate or close to the first end 102 of the needle 100 and the second end 124 being proximate or close to the second end 104 of the needle 100. As shown in FIG. 1, the open second end 124 is in the form of a vent port or opening that is formed in a side surface 103 of the body 101 as opposed to being formed directly at the second end 104. The vent port 124 is preferably formed in the side surface 103 either at or close to the second end 104 since the vent port 124 is to be in fluid communication with the bone marrow space when the distal end 104 of the needle 100 is inserted and guided to the bone marrow collection site (space). The open first end 122 is also formed in the side surface 103 either at or close to the first end 102 and is in the form of a vent port or opening that is in fluid communication with atmospheric air (pressure) when the needle 100 is properly used and the distal tip 104 is guided to the bone marrow site (space). Between the vent ports 122, 124, the second lumen 120 is defined by a longitudinal (linear) channel that is formed between an inner surface of the side surface or wall 103 and the partitioning wall 140. In order for the first opening 122 to serve as a vent port, the second lumen 120 is preferably closed at the first end 122 by a structure 150, such as wall that extends across the channel that defines, in part, the second lumen 120. The structure 150 does not extend across or in any way obstruct the first lumen 110 since the first lumen 110 is completely open at both ends to permit collection and withdrawal of the sample from the bone marrow space. The closing structure 150 is thus located proximate to the vent port 122. The distance between the two vent ports 122, 124 is such that when the distal second end 104 is guided and positioned at the bone marrow space, the vent port 122 is located outside or exterior to the patient and in fluid communication with atmospheric air.

Optionally and preferably in a number of applications, the needle 100 includes a filter 200 which is associated with the second lumen 120 to remove any physical or bacterial particles that might be drawn into the space (channel) during the procedure. The filter 200 can be placed in any number of different locations, including within and along the channel that extends between the first and second vent ports 120 or, as illustrated, the filter 200 can be placed in the first opening 122. By positioning the filter 200 at the first opening (vent port) 122, the filter 200 can easily be accessed and changed, inspected or replaced with a different type of filter 200. The filter 200 can be held within the vent port 122 using conventional techniques, including establishing a frictional fit between the filter 200 and the walls t of the vent port 122. The use of an adhesive material or other techniques can equally be used so long as the filter 200 is secured in place and air flowing between the vent ports 122, 124 passes through the filter 200.

While the double lumen type needle of FIG. 1 illustrates one exemplary needle construction, it will be appreciated that the needle 100 can have a number of different constructions and can be manufactured in a number of different ways. For example, the creation of the first and second lumens 110, 120 can result from inserting or forming a divider, such as wall 140, within a single lumen tube (body 101), resulting in the formation of double lumen. The divider is then sealed against the single lumen to maintain a vacuum therein. Alternatively, two single lumen tubes could be coupled together, as by a bonding or welding operation or adhesives, etc., to produce a double lumen tube. In yet another embodiment, a tube with a smaller diameter can be inserted into a tube with a larger diameter thereby producing a double lumen tube. Moreover, the inserted tube might not necessarily have to be made of stainless steel but instead could be constructed of a small diameter plastic tube, while the other tube could be constructed of a stainless steel to provide the stability for cortical puncture.

FIGS. 3–4 illustrate a needle 300 being used in combination with a stylet 400. The needle 300 is very similar to the needle 100 and therefore, like elements are numbered alike. In this embodiment, the relative areas of the first and second lumens 110, 120 are shown and more particularly, the first lumen 110 occupies significantly more cross-sectional area than the second lumen 120 since the first lumen 110 receives and permits aspiration of the sample to the collection chamber 170 (FIG. 1); while the second lumen 120 performs a venting action and only needs to permit air to pass therealong. The cross-sectional area of the second lumen 120 should be such that it does not produce a resistance to airflow and permits the desired venting action.

It will be appreciated that the ratio of the cross-sectional areas between the first and second lumens 110, 120 is variable depending upon the particular given application; however, the dimensions of the second lumen 120 is such that it does not produce a resistance to airflow but instead vents the air. For example, the cross-sectional area of the second lumen 120 compared to the entire cross-sectional area of the needle 100 can be on the order of between about 1% to about 40% in one embodiment, between 10%–30% in another embodiment; and 15%–25% in another embodiment. However, these values are merely exemplary in nature and are not limiting of the present scope of the present invention in any manner.

The stylet 400 as you know is placed within the needle 300 and has a tip to it which allows the needle 300 to puncture the cortex. The stylet 400 is removed once the needle 300 has penetrated the cortex opening up the first lumen 110 for the aspiration procedure. In this needle design, the stylet 400 will initially sit within the first lumen 110 that carries the material from the bone marrow to the syringe and not in the venting lumen (second lumen 120).

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. An aspirating needle for collecting a specimen comprising:
an elongated hollow body that includes a distal tip that is constructed to puncture cortical bone and a first lumen portion and a second lumen portion, the first lumen portion being open at both ends for placement at a specimen site to collect and permit aspiration of the specimen from the specimen site, the second lumen having first and second vent ports, with the second vent port being formed along the elongated body such that when the needle is placed at the specimen site, the second vent port is positioned at the specimen site, the first vent port being in fluid communication with atmospheric air when the needle is positioned at the specimen site so as to permit pressure within the specimen site to equilibrate with atmospheric pressure by means of the venting action of the second lumen portion, wherein the first and second vent ports are formed along axes that are perpendicular to a longitudinal axis that extends along the length of a main vent channel that connects the first and second vent ports to one another, and wherein only the opening of the first lumen portion is located at the distal tip, with the second vent port being offset therefrom, the first and second lumen portions being formed in a non-concentric arrangement and a cross-sectional area of the first lumen portion being greater than a cross-sectional area of the second lumen portion, the first lumen portion being linear along its length, the needle having a filter disposed within the second lumen to remove any physical or bacterial material that is drawn into the second lumen portion during an aspiration procedure.

2. The aspirating needle of claim 1, wherein the first and second vent ports are formed in a side wall of the needle body.

3. The aspirating needle of claim 1, wherein the first and second lumens are disposed adjacent one another and extend longitudinally side-by-side for at least a substantial length of the needle.

4. The aspirating needle of claim 1, wherein the body includes a partitioning structure that extends longitudinally therein and divides an interior of the body into the first and second lumen portions.

5. The aspirating needle of claim 1, wherein the needle includes a sharp distal end with the first lumen portion being open at the distal end.

6. The aspirating needle of claim 1, wherein a ratio between a cross-sectional area of the second lumen portion relative to a cross-sectional area of the entire needle is between about 0.01 and 0.4.

7. The aspirating needle of claim 1, wherein a distal end portion of the hollow body comprises a sharp beveled edge with the first lumen portion being open at a distal tip of the distal end portion, with the second vent port being spaced from the distal tip such that the opening of the first lumen portion is a distalmost opening of the needle.

8. The aspirating needle of claim 1, wherein the filter is disposed and retained in the first vent port formed in a side wall of the second lumen of the needle.

* * * * *